United States Patent [19]

Sasaki et al.

[11] Patent Number: 5,166,448
[45] Date of Patent: Nov. 24, 1992

[54] INTERMEDIATE FOR PREPARING FLUORINE-SUBSTITUTED COMPOUND CONTAINING ETHER BOND

[75] Inventors: Makoto Sasaki, Saitama; Haruyoshi Takatsu; Kiyofumi Takeuchi, both of Tokyo, all of Japan

[73] Assignee: Dainippon Ink & Chemicals, Inc., Tokyo, Japan

[21] Appl. No.: 709,842

[22] Filed: Jun. 4, 1991

Related U.S. Application Data

[62] Division of Ser. No. 557,336, Jul. 26, 1990, Pat. No. 5,068,462.

[30] Foreign Application Priority Data

| Jul. 28, 1989 | [JP] | Japan | 1-196074 |
|---|---|---|---|
| Oct. 9, 1989 | [JP] | Japan | 1-262225 |
| Dec. 18, 1989 | [JP] | Japan | 1-326165 |
| Jan. 25, 1990 | [JP] | Japan | 2-15481 |
| Apr. 16, 1990 | [JP] | Japan | 2-97648 |
| May 8, 1990 | [JP] | Japan | 2-116924 |

[51] Int. Cl.[5] .......................... C07C 49/403
[52] U.S. Cl. .................... 568/367; 568/376
[58] Field of Search ................. 568/367, 376

[56] References Cited

PUBLICATIONS

Acton et al., "Sweeteners based on syn oximes of 4-(-methoxy substituted)-1-cyclohexene-1-carboxaldehydes", *Chem. Abstracts*, 81(21) 135544y.

Musso et al., "Asteranes. IV. Syntheses of Norpinanes (bicyclo-3.1.1. heptanes," *Chemical Abstracts,* 68 (3) 12514n.

*Chemical Abstracts Formula Index,* vol. 68, 1968.

*Primary Examiner*—Marianne M. Cintins
*Assistant Examiner*—Margaret J. Argo
*Attorney, Agent, or Firm*—Armstrong & Kubovcik

[57] ABSTRACT

A fluorine-substituted compound containing an ether bond and an intermediate thereof are described, which are represented by:

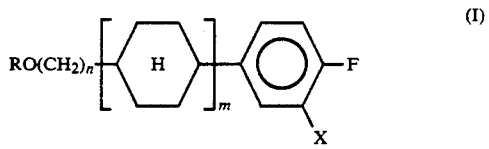

(I)

wherein R represents a straight-chain alkyl group having 1 to 8 carbon atoms; n represents an integer of 2 to 7; m represents 1 or 2, X represents a hydrogen atom or a fluorine atom, and

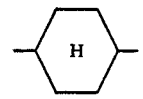

represents a trans-(equatorial-equatorial)cyclohexane ring.

A compound represented by formula (II):

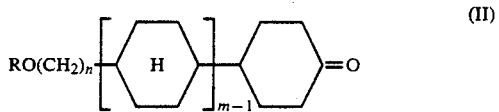

(II)

wherein R represents a straight-chain alkyl group having 1 to 8 carbon atoms; n represents an integer of 2 to 7; m represents 1 or 2,

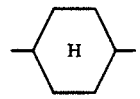

represents a trans-(equatorial-equatorial)cyclohexane ring.

3 Claims, No Drawings

INTERMEDIATE FOR PREPARING FLUORINE-SUBSTITUTED COMPOUND CONTAINING ETHER BOND

This is a division of application Ser. No. 07/557,336 filed Jul. 26, 1990, now U.S. Pat. No. 5,068,462.

FIELD OF THE INVENTION

The present invention relates to a fluorine-substituted compound containing an ether bond useful as an electrooptical display material and an intermediate thereof.

BACKGROUND OF THE INVENTION

Typical examples of liquid crystal cell include a field effect mode cell proposed by M. Schadt et al, APPLIED PHYSICS LETTERS, 18, 127-128 (1971), a dynamic scattering mode cell proposed by G.H. Heilmeier et al, PROCESSING OF THE I.E.E.E., 56, 1162-1171 (1968) and a guest/host mode cell proposed by G.H. Heilmeier et al, APPLIED PHYSICS LETTERS, 13, 91 (1968) or D.L. White et al, JOURNAL OF APPLIED PHYSICS, 45, 4718 (1978).

Among these liquid crystal display cells, TN mode cells, which belong to the field effect mode cells, are majorly used at present. In the case of the TN mode cells, it is required to set the product of the optical anisotropy ($\Delta n$) of the liquid crystal material in the cell and the thickness (d; $\mu m$) of the cell to a definite value in order to achieve good cell appearance, as indicated by G. Bauer, *Mol. Cryst. Liq. Cryst.*, 63, 45 (1981). A liquid crystal display cell used in practice has a $\Delta n.d$ value of either 0.5, 1.0, 1.6 or 2.2. Generally speaking, the visual properties of a liquid crystal display cell can be improved by setting the $\Delta n.d$ value to 0.5. On the other hand, the frontal contrast thereof can be improved by setting the $\Delta n.d$ value to 1.0, 1.6 or 2.2. Therefore, it is generally recommended to set the $\Delta n.d$ value of a liquid crystal display cell to 0.5, when it is regarded as important to achieve excellent visual properties from any direction. On the other hand, the $\Delta n.d$ value thereof may be preferably set to 1.0, 1.6 or 2.2 in order to obtain a clear frontal contrast.

On the other hand, the thickness of a liquid crystal cell layer in a practically used liquid crystal display cell is commonly set to a definite value within a limited range of 6 to 10 $\mu m$. Thus, a liquid crystal material having a low $\Delta n$ value is required in order to set the $\Delta n.d$ value to 0.5. In contrast thereto, a liquid crystal material having a high $\Delta n$ value is required in order to set the $\Delta n.d$ value to 1.0, 1.6 or 2.2. Namely, either a liquid crystal material having a low $\Delta n$ value or one having a high $\Delta n$ value is required depending on the desired display properties.

In the case of the TN mode cells, the dielectric anisotropy ($\Delta \epsilon$) of a mixed liquid crystal is required to be positive. Therefore, it is demanded to provide nematic liquid crystal materials which have large $\Delta \epsilon$ values and a low threshold voltage and can drive at low voltage.

SUMMARY OF THE INVENTION

An object of the present invention is to provide a novel compound having a low $\Delta n$ value, a large $\Delta \epsilon$ value, and a low threshold voltage and an intermediate thereof.

In order to achieve the object, the present invention provides a compound represented by formula (I):

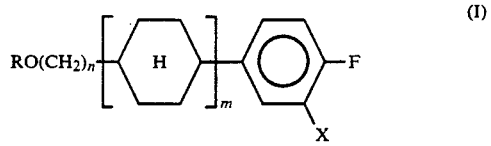

wherein R represents a straight-chain alkyl group having 1 to 8 carbon atoms; n represents an integer of 2 to 7; m represents 1 or 2, X represents a hydrogen atom or a fluorine atom, and each

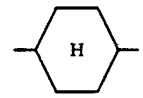

ps represents a trans-(equatorial-equatorial)cyclohexane ring; and an intermediate of the compound of formula (I) represented by formula (II):

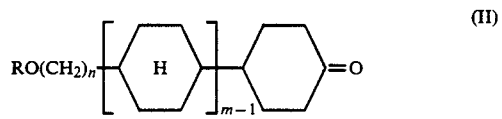

wherein R represents a straight-chain alkyl group having 1 to 8 carbon atoms; n represents an integer of 2 to 7; m represents 1 or 2,

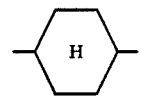

represents a trans-(equatorial-equatorial)cyclohexane ring.

DETAILED DESCRIPTION OF THE INVENTION

The compounds represented by formula (I) and formula (II) according to the present invention can be prepared, for example, by the following manufacturing procedure:

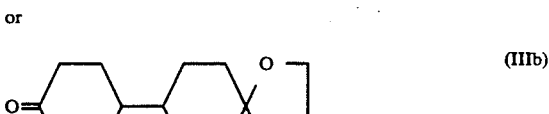

or

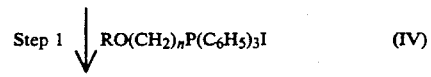

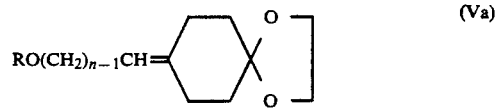

or

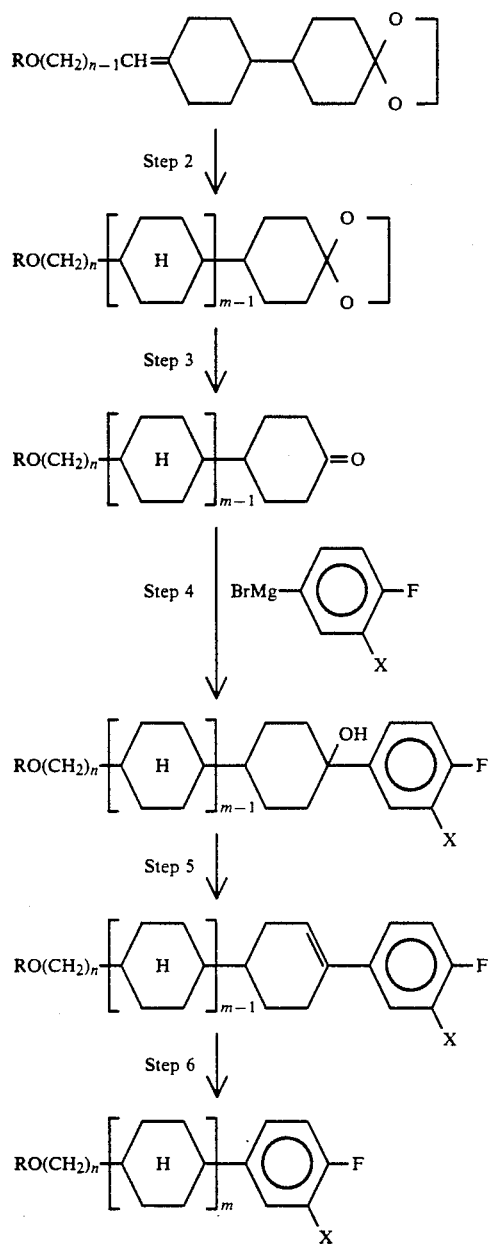

wherein R represents a straight-chain alkyl group having 1 to 8 carbon atoms, n represents an integer of 2 to 7, m represents 1 or 2, X represents a hydrogen atom or fluorine atom, and

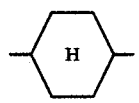

represents a trans-(equatorial-equatorial)cyclohexane ring.

Step 1

A compound of formula (IV) is treated with a strong base, e.g., potassium t-butoxide in tetrahydrofuran to obtain an ylide compound. The obtained compound is reacted with a compound of formula (IIIa) or (IIIb) to obtain a compound of formula (Va) or (Vb).

Step 2

The compound of formula (Va) or (Vb) is catalytically reduced in ethyl acetate in the presence of Raney nickel as a catalyst to obtain a compound of formula (VI).

Step 3

The compound of formula (VI) is hydolyzed in toluene-diluted sulfuric acid to obtain the compound of formula (II) according to the present invention.

Step 4

The compound of formula (II) is reacted with a grignard reagent of formula (VII) in tetrahydrofuran to obtain a compound of formula (VIII).

Step 5

The compound of formula (VIII) is dehydrated in toluene in the presence of an acid catalyst, e.g., p-toluenesulfonic acid to obtain a compound of formula (IX).

Step 6

The compound of formula (IX) is catalytically reduced in an alcohol, e.g., ethanol, in the presence of Raney nickel as a catalyst to obtain a compound of formula (I) according to the present invention.

In formula (I), a compound wherein n is 1 can also be prepared by the following manufacturing procedure.

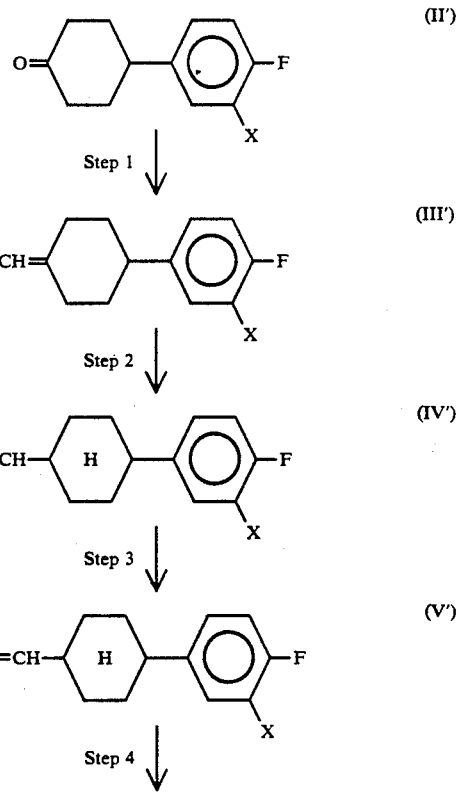

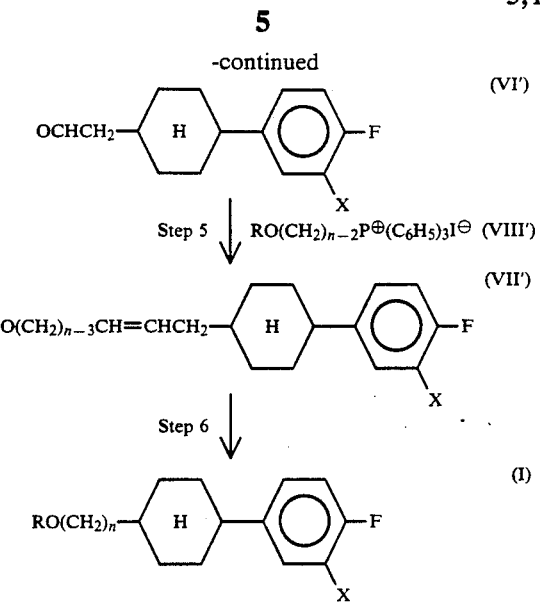

wherein R represents a straight-chain alkyl group having 1 to 8 carbon atoms, n represents an integer of 2 to 7, represents a trans(equatorial-equatorial)-cyclohexane ring, and X represents a fluorine or hydrogen atom.

Step 1

A compound of formula (II') is reacted with methoxymethyltriphenyl phosphonium chloride in t-butyl methyl ether to obtain a compound of formula (III').

Step 2

The compound of formula (III') is treated with hydrochloric acid in tetrahydrofuran to obtain a compound of formula (IV').

Step 3

The compound of formula (IV') is reacted with methoxymethyltriphenyl phosphonium chloride in t-butyl methyl ether to obtain a compound of formula (V').

Step 4

The compound of formula (V') is treated with hydrochloric acid in tetrahydrofuran to obtain a compound of formula (VI').

Step 5

The compound of formula (VIII') is treated with a strong base, e.g., potassium tert-butoxide in tetrahydrofuran to obtain an ylide compound. The obtained compound is reacted with the compound of formula (VI') to obtain a compound of formula (VII').

Step 6

The compound of formula (VII') is catalytically reduced in ethyl acetate in the presence of Raney nickel as a catalyst to obtain the compound of formula (I) according to the present invention.

Phase transition temperatures of typical compounds of formula (I) thus obtained are listed in Table 1 below.

TABLE 1

$$RO(CH_2)_n-\left[\underset{H}{\bigcirc}\right]_m-\underset{X}{\bigcirc}-F$$

| Compound No. | R | n | m | X | Phase Transition Temperature (°C.) |
|---|---|---|---|---|---|
| 1 | CH$_3$— | 3 | 1 | H— | 27 (C⟶I) |
| 2 | CH$_3$— | 3 | 1 | F— | 12 (C⟶I) |
| 3 | CH$_3$— | 5 | 1 | H— | 44 (C⟶I) |
| 4 | CH$_3$— | 5 | 1 | F— | 23 (C⟶I) |
| 5 | CH$_3$— | 2 | 2 | H— | 49 (C⟶N) |
|   |   |   |   |   | 82 (N⟶I) |
| 6 | CH$_3$— | 2 | 2 | F— | 72 (C⟶N) |
|   |   |   |   |   | 129 (N⟶I) |
| 7 | CH$_3$— | 3 | 2 | H— | 85 (C⟶N) |
|   |   |   |   |   | 153 (N⟶I) |
| 8 | CH$_3$— | 3 | 2 | F— | 61 (C⟶N) |
|   |   |   |   |   | 108 (N⟶I) |
| 9 | CH$_3$— | 5 | 2 | F— | <Room Temp. (C⟶S) |
|   |   |   |   |   | 40 (S⟶N) |
|   |   |   |   |   | 107 (N⟶I) |

Note: In Table 1, C represents a crystalline phase; N represents a nematic phase; and I represents an isotropic liquid phase.

The compounds of formula (I) according to the present invention are nematic liquid crystal compounds having a positive dielectric anisotropy. Thus it may be mixed with other nematic liquid crystal compound(s) having a negative dielectric anisotropy and applied for a dynamic scattering mode display cell material. Alternatively, it may be mixed with other nematic liquid crystal compound(s) having a positive or negative dielectric anisotropy and applied for a field effect mode display cell material.

Typical examples of the compounds which can be preferably mixed with the compound of formula (I) include, for example, 4-substituted benzoic acid 4'-substituted phenyl esters, 4-substituted cyclohexane-carboxylic acid 4'-substituted phenyl esters, 4-substituted cyclohexanecarboxylic acid 4'-substituted biphenyl esters, 4-(4-substituted cyclohexanecarbonyl-oxy)benzoic acid 4'-substituted phenyl esters, 4 (4-substituted cyclohexyl)benzoic acid 4'-substituted phenyl esters, 4-(4-substituted cyclohexyl)benzoic acid 4'-substituted cyclohexyl esters, 4-substituted 4'-substituted biphenyls, 4-substituted phenyl-4'-substituted cyclohexanes, 4-substituted 4''-substituted terphenyls, 4-substituted biphenyl 4'-substituted cyolohexanes, 2-(4 substituted phenyl)-5-substituted pyrimidines.

Table 2 shows $\Delta n$, $\Delta \epsilon$, and the visoosity (c.p.) at 20° C., and the threshold voltage of each liquid crystal mixture comprising 80% by weight of a mixed liquid crystal (A) which is widely employed in practice as a nematic liquid crystal material and a matrix liquid crystal and 20% by weight of the compounds of formula (I), Nos. 1 to 4, shown in Table 1 and the compound (a), (b) or (c) shown below which is similar to the compound of the invention in structure and has low $\Delta n$ and positive $\Delta \epsilon$. For comparison, those of the mixed liquid crystal (A) are also shown in Table 3.

The mixed liquid crystal (A comprises:

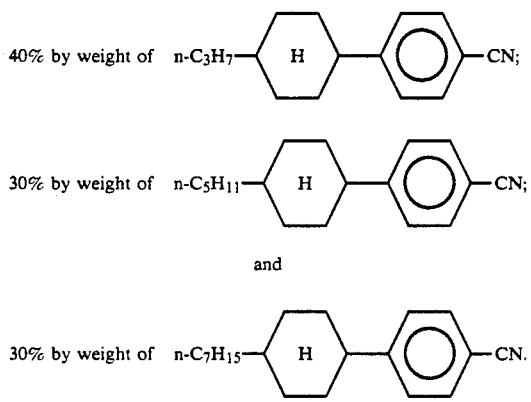

The compounds (a), (b) and (c) are represented by the following formulae.

TABLE 2

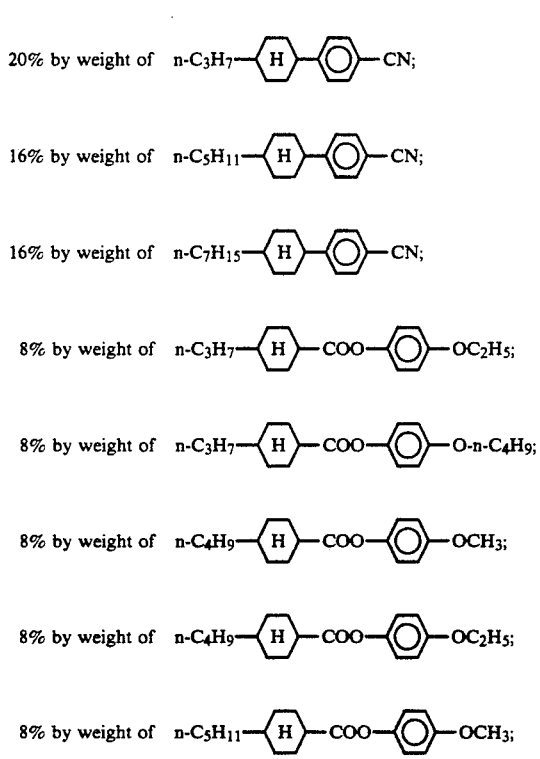

| Liquid Crystal Mixture | $\Delta n$ | $\Delta \epsilon$ | Threshold Voltage (V) | Viscosity |
|---|---|---|---|---|
| (A) | 0.117 | 12.0 | 1.51 | 22.0 |
| (A) + No. 1 | 0.107 | 11.5 | 1.20 | 19.4 |
| (A) + No. 2 | 0.102 | 10.9 | 1.01 | 20.1 |
| (A) + No. 3 | 0.104 | 10.9 | 1.26 | 19.4 |
| (A) + No. 4 | 0.106 | 11.5 | 1.15 | 21.2 |
| (A) + (a) | 0.110 | 10.1 | 1.53 | 20.2 |
| (A) + (b) | 0.110 | 10.4 | 1.36 | 19.2 |
| (A) + (c) | 0.109 | 10.3 | 1.38 | 20.1 |

It can be understood that the compounds of formula (I) decrease the viscosity of the matrix liquid crystal and, as compared to the compounds having a similar structure, decreases $\Delta n$ and remarkably decreases the threshold voltage without a large decrease in $\Delta \epsilon$ of the matrix liquid crystal (A).

These superiorities are clear with respect to decrease in the threshold voltage when the compounds of formula (I) are compared with the compound (a) which is widely employed in practice and compounds (b) and (c) which are similar to the compound of the invention in structure.

Table 3 shows $\Delta n$, $\Delta \epsilon$ and the threshold voltage of each liquid crystal mixture comprising 80% by weight of a mixed liquid crystal (B) which is widely employed in practice as a nematic liquid crystal material and a matrix liquid crystal and 20% by weight of the compounds of formula (I), Nos. 5 to 9 shown in Table 1 and the compound (d) or (e) shown below which is similar to the compound of the invention in structure and has low $\Delta n$ and positive $\Delta \epsilon$. For comparison, those of the mixed liquid crystal (A) are also shown in Table 3.

The mixed liquid crystal (B) comprises:

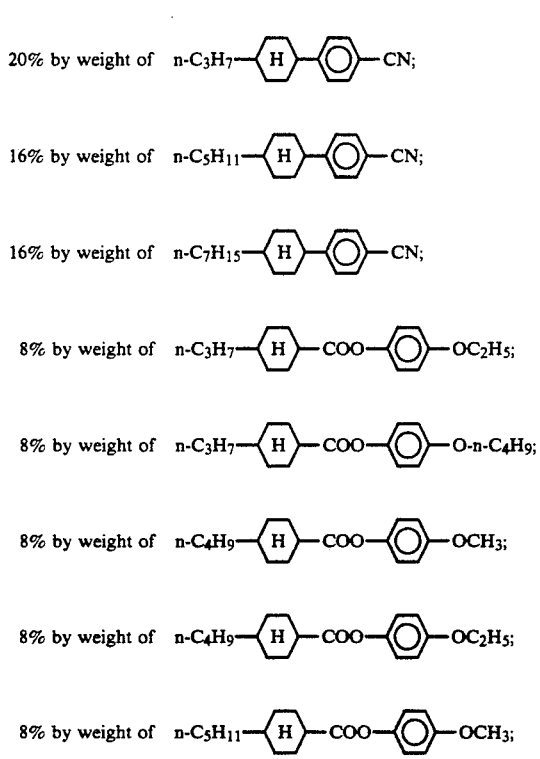

and

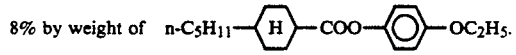

The compounds (d) and (e) are a known compound as described in U.S. Pat. No. 4,405,488 and represented by the following formulae:

TABLE 3

(d) n-C5H11—[H]—[H]—[⌬]—F, F (e) n-C7H15—[H]—[H]—[⌬]—F, F

| Liquid Crystal Mixture | Δn | Δε | Threshold Voltage (V) |
|---|---|---|---|
| (B) | 0.092 | 6.7 | 1.60 |
| (B) + No. 5 | 0.089 | 7.0 | 1.54 |
| (B) + No. 6 | 0.093 | 6.8 | 1.74 |
| (B) + No. 7 | 0.091 | 7.1 | 1.49 |
| (B) + No. 8 | 0.096 | 6.8 | 1.70 |
| (B) + No. 9 | 0.091 | 7.0 | 1.50 |
| (B) + (d) | 0.096 | 6.2 | 1.92 |
| (B) + (e) | 0.096 | 6.3 | 1.91 |

It can be understood that the compound of formula (I) lowers Δn, remarkably lowers the threshold voltage without so much increase in Δn, or increases Δε without so much change in Δn of the liquid crystal mixtures.

The effect of the invention is apparent from that the conventionally known compounds (d) and (e) increase Δn, lower Δε, and remarkably increase the threshold voltage of the liquid crystal mixtures.

The compounds of formula (I) according to the present invention have large Δε and low threshold voltage, and when mixed with a nematic liquid crystal which is widely used in practice as a matrix liquid crystal, the compounds of the invention lower Δn, increase Δε, and lower the threshold voltage of the liquid crystal mixture, as compared to the compound which has a similar structure of the invention's.

The compounds of formula (I) according to the present invention have remarkable effects as compared to a known compound which has a similar structure of the invention's, have excellent visual properties, and are very useful as materials for TN mode liquid crystal display cells which can drive at low voltage.

The compounds of formula (II) according to the present invention is very useful as an intermediate for synthesizing various liquid crystal, compounds such as the compounds of formula (II).

The present invention is now illustrated in greater detail by reference to the following non-limiting examples.

EXAMPLE 1

324 g (0.7 mol) of $CH_3OCH_2CH_2CH_2P^{\oplus}(C_6H_5)_3I^{\ominus}$ was added to 1 liter of tetrahydrofuran and the solution was cooled to $-4°$ C. To the solution, 90 g (0.8 mol) of potassium t-butoxide was added for 10 minutes, and reacted at the same temperature for 10 minutes and at room temperature for 1 hour. After cooling the reaction solution to $-5°$ C., a solution of 119 g (0.5 mol) of the following compound:

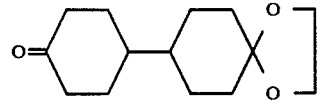

dissolved in 500 ml of tetrahydrofuran was added thereto for 15 minutes, and the resulting solution was reacted at the same temperature for 10 minutes and at room temperature for 2 hours. After the reaction, to the reaction mixture was added 1 liter of water, extracted twice with 1 liter of ethyl acetate. After the extract was washed with water and dried, the solvent was distilled off under reduced pressure to obtain a residue. After the residue was dissolved by heat in 500 ml of toluene, 500 ml of n-hexane was added thereto and the resulting solution was allowed to stand overnight. The precipitated crystal was filtered off and the filtrate was purified by chromatography on silica gel to obtain 131 g (0.45 mol) of the following compound:

$CH_3OCH_2CH_2CH_2$=[⌬]—[⌬]⟨O,O]

131 g (0.45 mol) of this compound was dissolved in 1 liter of ethyl acetate and the solution was catalytically reduced in the presence of Raney nickel as a catalyst. After the reaction, the catalyst was separated by filtration, and the solvent was removed from the filtrate by distillation under reduced pressure to obtain 124 g (0.42 mol) of the following compound:

$CH_3OCH_2CH_2CH_2$—[H]—[⌬]⟨O,O]

124 g (0.42 mol) of this compound was dissolved in 800 ml of toluene, and 400 ml of 16% sulfuric acid was added thereto, followed by heating under reflux for 14 hours. After the reaction, the reaction solution was subjected to separation, and the organic layer was washed with water and dried. The solvent was removed from the organic layer by distillation under reduced pressure to obtain a residue. The residue was purified by recrystallization from n-hexane to obtain 80 g (0.32 mol) of the following compound:

$CH_3OCH_2CH_2CH_2$—[H]—[⌬]=O

Melting point: 38° C.

EXAMPLE 2

100 g of (0.22 mol) of $CH_3OCH_2CH_2CH_2P(C_6H_5)_3I$ was added to 350 ml of tetrahydrofuran and the solution was cooled to $-4°$ C. To the solution, 33.6 g (0.3 mol) of potassium t-butoxide was added for 10 minutes, and reacted at the same temperature for 10 minutes and at room temperature for 1 hour. After cooling the reaction solution to −5° C., a solution of 23.4 g (0.15 mol) of the following compound:

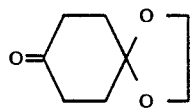

dissolved in 70 ml of tetrahydrofuran was added thereto for 15 minutes, and the resulting solution was reacted at the same temperature for 10 minutes and at room temperature for 2 hours. After the reaction, to the reaction mixture was added 1 liter of water, extracted twice with 200 ml of ethyl acetate. After the extract was washed with water and dried, the solvent was removed by distillation under reduced pressure to obtain a residue. After the residue was dissolved by heat in 200 ml of toluene, 200 ml of n-hexane was added thereto and the resulting solution was allowed to stand overnight. The precipitated crystal was filtered off and the filtrate was purified by chromatography on silica gel to obtain 21 g (0.1 mol) of the following compound:

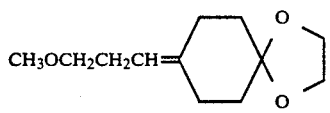

21 g (0.1 mol) of this compound was dissolved in 250 ml of ethyl acetate and the solution was catalytically reduced in the presence of Raney nickel as a catalyst. After the reaction, the catalyst was separated by filtration, and the solvent was removed from the filtrate by distillation under reduced pressure to obtain 20 g (0.094 mol) of the following compound:

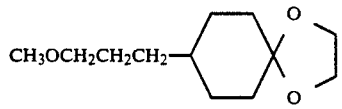

20 g (0.094 mol)of this compound was dissolved in 200 ml of toluene, and 100 ml of 16% sulfuric acid was added thereto, followed by heating under reflux for 14 hours. After the reaction, the reaction solution was subjected to separation, and the organic layer was washed with water and dried. The solvent was removed from the organic layer by distillation under reduced pressure to obtain a residue. The residue was further distilled off under reduced pressure to obtain 14 g (0.082 mol) of the following compound.

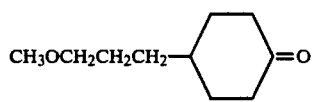

bp$_{15}$: 129–132° C.

EXAMPLE 3

1.5 g (0.06 mol) of magnesium powder was added to 10 ml of absolute tetrahydrofuran and the mixture was activated by a catalytic amount of dibromoethylene. Then to the mixture was dropwise added a solution of 11.6 g (0.06 mol) of the compound of formula:

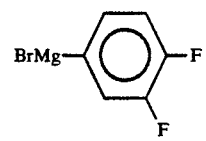

diluted in 25 ml of absolute tetrahydrofuran at 30° C. or lower. After the dropwise addition, stirring of the mixture was continued for 30 minutes at the same temperature. After the reaction, to the reaction solution was dropwise added a solution of 10.6 g (0.045 mol) of the compound obtained in Example 1 dissolved in 30 ml of tetrahydrofuran at 25° C. or lower, and reacted for 3 hours at room temperature.

After the reaction, the reaction mixture was added to 50 ml of 9% hydrochloric acid, and extracted thrice with 100 ml of toluene. After the extract was washed with water and dried, the solvent was removed by distillation under reduced pressure to obtain 15.2 g (0.044 mol) of the following compound:

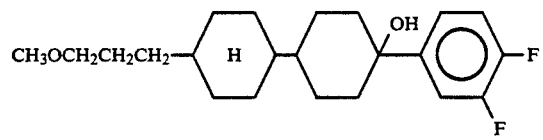

15.2 g of this compound was dissolved in 250 ml of toluene and 1 g of p-toluenesulfonic acid was added thereto, followed by heating under reflux for 4 hours while dewatering by a dewatering apparatus.

After the reaction, the toluene phase was washed with water and dried. Then the solvent was removed from the toluene layer by distillation under reduced pressure to obtain a residue. The residue was purified by recrystallization from 130 ml of ethanol to obtain 13.0 g (0.039 mol) of the following compound:

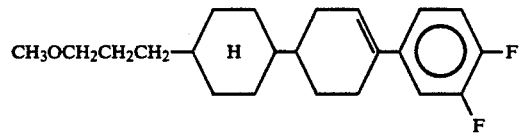

13.0 9 of this compound was dissolved in 250 ml of ethanol and 1 g of Raney nickel was added thereto, followed by catalytical reduction under hydrogen pressure of 5 kg/cm$^2$ for 15 hours at room temperature. After the reaction, the catalyst was separated by filtration and the ethanol was distilled off under reduced temperature to obtain a residue. The residue was purified by recrystallization from 80 ml of n-hexane to obtain 8.4 g (0.025 mol) of the following compound:

CH₃OCH₂CH₂CH₂―⟨H⟩―⟨H⟩―⟨O⟩―F
                              |
                              F

Phase transition temperature: 61° C.
(C ⟶ N)
108° C.
(N ⇌ I)

EXAMPLE 4

A compound of the following formula was obtained in the same manner as in Example 3.

CH₃OCH₂CH₂CH₂―⟨H⟩―⟨H⟩―⟨O⟩―F

Phase transition temperature: 85° C.
(C ⟶ N)
153° C.
(N ⇌ I)

EXAMPLE 5

A compound of the following formula was obtained in the same manner as in Example 3.

CH₃OCH₂CH₂―⟨H⟩―⟨H⟩―⟨O⟩―F
                          |
                          F

Phase transition temperature: 72° C.
(C ⟶ N)
129° C.
(N ⇌ I)

EXAMPLE 6

A compound of the following formula was obtained in the same manner as in Example 3.

CH₃OCH₂CH₂―⟨H⟩―⟨H⟩―⟨O⟩―F

Phase transition temperature: 49° C.
(C ⟶ N)
82° C.
(N ⇌ I)

EXAMPLE 7

A compound of the following formula was obtained in the same manner as in Example 3.

CH₃OCH₂CH₂CH₂CH₂CH₂―⟨H⟩―⟨H⟩―⟨O⟩―F
                                  |
                                  F

Phase transition temperature:
not higher than room temperature (C ⟶ S)
40° C. (S ⇌ N)
107° C. (N ⇌ I)

EXAMPLE 8

44.5 g (0.13 mol) of methoxymethyl triphenyl phosphonium chloride was suspended in 150 ml of t-butylmethylether and while maintaining the internal temperature of the solution at −10° C., the solution was treated with 16.8 g (0.15 mol) of potassium t-butoxide within 5 minutes. After stirring for 10 minutes at the same temperature, stirring of the resulting solution was continued for 1 hour at room temperature. While maintaining the internal temperature to −10° C., a solution of 19.2 g (0.1 mol) of the compound of formula:

O=⟨  ⟩―⟨O⟩―F in 50 ml of tetrahydrofuran was dropwise added to the solution for 5 minutes, followed by stirring at the same temperature for 10 minutes and at room temperature for 1 hour.

After the reaction, to the reaction solution was added 150 ml of water, and the solution was stirred for 10 minutes and extracted twice with 150 ml of ethyl acetate. After the extract was washed and dried, the solvent was distilled off under reduced pressure to obtain a residue. To the residue a mixed solvent of n-hexane/toluene (1/1 by volume) and after stirring for 30 minutes, triphenylphosphine oxide was filtered out. The filtrate was purified by chromatography on silica gel to obtain 20 g (0.09 mol) of the following compound:

CH₃OCH=⟨  ⟩―⟨O⟩―F 20 g of this compound is dissolved in a mixed solvent of 100 ml of tetrahydrofuran and 20 ml of 9% hydrochloric acid and the solution was heated under reflux for 1 hour. After the reaction, to the reaction solution was added 200 ml of water and extracted twice with 150 ml of ethyl acetate. After the extract was washed with water and dried, the solvent was distilled off under reduced pressure to obtain 16 g (0.078 mol) of the following compound:

OCH=⟨  ⟩―⟨O⟩―F 44.5 g (0.13 mol) of methoxymethyl triphenyl phosphonium chloride was suspended in 150 ml of t-butyl methyl ether and while maintaining the internal temperature of the solution to −10° C., the solution was treated with 16.8 g (0.15 mol) of potassium t-butoxide within 5 minutes, followed by stirring for 10 minutes at the same temperature and for 1 hour at room temperature. Next, while maintaining the internal temperature at −10° C., a solution of 16 g of the above-noted compound in 50 ml of tetrahydrofuran was dropwise added to the solution within 5 minutes, followed by stirring at the same temperature for 10 minutes and at room temperature for 1 hour. After the reaction, to the reaction solution was added 150 ml of water, and the resulting solution stirred for 10 minutes and extracted twice with 150 ml of ethyl acetate. After the extract was washed with water and dried, the solvent was distilled off under reduced pressure to obtain a residue. To the residue 500 ml of a mixed solvent of n-hexane/toluene (1/1 by volume) was added and after stirring for 30 minutes, triphenylphosphine oxide was filtered out. The filtrate was purified by chromatography on silica gel to obtain 18 g (0.077 mol) of the following compound:

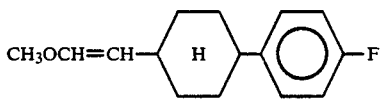

18 g of this compound is dissolved in a mixed solvent of 100 ml of tetrahydrofuran and 20 ml of 9% hydrochloric acid and the solution was reflux for 1 hour. Next, to the reaction solution was added 20 ml of water and extracted twice with 150 ml of ethyl acetate. After the extract was washed with water and dried, the solvent was distilled off under reduced pressure to obtain 15 g (0.068 mol) of the following compound:

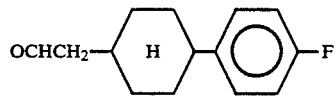

44.5 g (0.13 mol) of methoxymethyl triphenyl-phosphonium phosphonium chloride was suspended in 150 ml of t-butyl methyl ether and while maintaining the internal temperature of the solution to −10° C., the solution was treated with 16.8 g (0.15 mol) of potassium t-butoxide within 5 minutes, followed by stirring at the same temperature for 10 minutes and at room temperature for 1 hour. Next, while maintaining the internal temperature at −10° C., a solution of 15 g of the above-noted compound in 50 ml of tetrahydrofuran was dropwise added to the solution for 5 minutes, followed by stirring at the same temperature for 10 minutes. After the reaction, to the reaction solution was added 150 ml of water and the resulting solution was stirred for 10 minutes and extracted twice with 150 ml of ethyl acetate. After the extract wa washed with water and dried, the solvent was distilled off under reduced pressure to obtain a residue. To the residue, a mixed solvent of n-hexane/toluene (1/1 by weight) was added and after stirring for 30 minutes, triphenylphosphine oxide was filtered out. The filtrate was purified by chromatography on silica gel to obtain 16 g of the following compound:

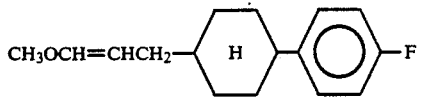

16 g of this compound was dissolved in 300 ml of ethyl acetate and the resulting solution was catalytically reduced in the presence of Raney nickel as a catalyst under hydrogen pressure of 5 kg/cm$^2$ for 10 hours. After the reaction, the catalyst was filtered out and the filtrate was distilled off under reduced pressure to obtain a residue. After the residue was distilled off under reduced pressure, the resulting residue was purified by recrystallization from methanol to obtain 12 g (0.048 mol) of the following compound:

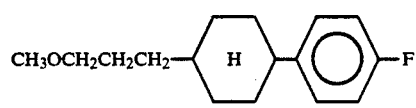

Melting point: 27° C.

EXAMPLE 9

17.0 g (0.1 mol) of the compound obtained in Example 2 was dissolved in 100 ml of absolute tetrahydrofuran. To the mixture was dropwise added a solution of 26 g (0.12 mol) of the compound of formula:

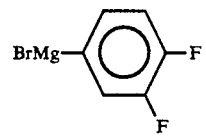

in 80 ml of absolute tetrahydrofuran at 25° C. or lower. After the dropwise addition, the resulting solution was reacted for 2 hours at room temperature. Next, after the addition of 100 ml of 9% hydrochloric acid, the resulting solution was extracted twice with 150 ml of ethyl acetate. Then, after the reaction solution was washed with water and dried, the solvent was distilled off under reduced pressure to obtain 25.6 g (0.09 mol) of the following compound:

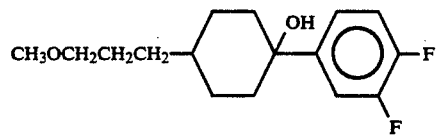

25.6 9 (0.09 mol) of this compound was dissolved in 250 ml of toluene and 1 g of p toluenesulfonic acid was added thereto, followed by heating under reflux for 2 hours while dewatering by a dewatering apparatus.

After the reaction, the toluene phase was washed with water and dried. Thereafter, the solvent was removed from the toluene by distillation under reduced pressure to obtain 19.4 g (0.085 mol) of the following compound:

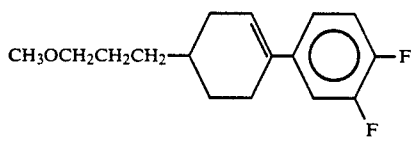

19.4 g (0.085 mol) of this compound was dissolved in 200 ml of ethyl acetate and 2 g of Raney nickel as a catalyst was added thereto, followed by catalytical reduction. After the reaction, the catalyst was removed from the reaction solution and the solvent was distilled off under reduced pressure to obtain a residue. The resulting residue was purified by recrystallization from 50 ml of ethanol to obtain 13.5 g (0.057 mol) of the following compound:

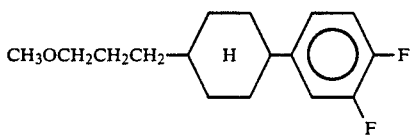

Melting point: 12° C.

EXAMPLE 10

A compound of the following formula was obtained in the same manner as in Example 8.

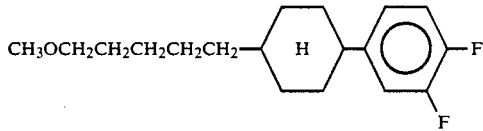

Melting point: 23° C.

EXAMPLE 11

A compound of the following formula was obtained in the same manner as in Example 8.

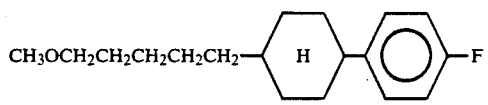

Melting point: 44° C.

While the invention has been described in detail and with reference to specific embodiments thereof, it will be apparent to one skilled in the art that various changes and modifications can be made therein without departing from the spirit and scope thereof.

What is claimed is:

1. A compound represented by formula (II):

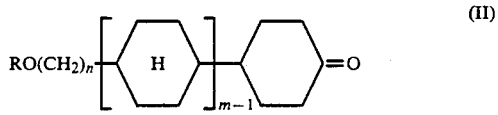

wherein R represents a straight-chain alkyl group having 1 to 8 carbon atoms; n represents an integer of 2 to 7; m represents 1 or 2; and

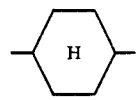

represents a trans-(equatorial-equatorial)cyclohexane ring.

2. A compound as claimed in claim 1, wherein m is 1.
3. A compound as claimed in claim 1, wherein m is 2.

* * * * *